United States Patent
Sparks et al.

(10) Patent No.: US 7,823,445 B2
(45) Date of Patent: Nov. 2, 2010

(54) SYSTEM AND METHOD OF ASSESSING A PROPERTY OF A FLOWING FLUID

(75) Inventors: Douglas Ray Sparks, Whitmore Lake, MI (US); Richard Thayre Smith, Saline, MI (US); Nader Najafi, Ann Arbor, MI (US)

(73) Assignee: Integrated Sensing Systems, Inc., Ypsilanti, MI (US)

( * ) Notice: Subject to any disclaimer, the term of this patent is extended or adjusted under 35 U.S.C. 154(b) by 20 days.

(21) Appl. No.: 12/329,871

(22) Filed: Dec. 8, 2008

(65) Prior Publication Data
US 2009/0145198 A1 Jun. 11, 2009

Related U.S. Application Data

(60) Provisional application No. 61/005,677, filed on Dec. 7, 2007.

(51) Int. Cl.
*G01F 1/68* (2006.01)
(52) U.S. Cl. .................................. 73/204.26
(58) Field of Classification Search ............ 73/862.59, 73/862.61, 862.621, 204.26, 204.25, 204.23, 73/861.355, 861.04
See application file for complete search history.

(56) References Cited

U.S. PATENT DOCUMENTS

| | | | |
|---|---|---|---|
| 6,308,553 B1 | 10/2001 | Bonne et al. | |
| 6,477,901 B1 | 11/2002 | Tadigadapa et al. | |
| 6,647,778 B2 | 11/2003 | Sparks | |
| 7,228,735 B2 | 6/2007 | Sparks et al. | |
| 7,263,882 B2 * | 9/2007 | Sparks et al. | 73/204.26 |
| 2006/0213552 A1 | 9/2006 | Sparks et al. | |

\* cited by examiner

*Primary Examiner*—Jewel Thompson
(74) *Attorney, Agent, or Firm*—Hartman & Hartman, P.C.; Gary M. Hartman; Domenica N. S. Hartman

(57) ABSTRACT

A fluid sensing system and method for sensing properties of a flowing fluid. The system and method entail a microfluidic device having a micromachined tube supported above a substrate, a tube passage within a freestanding portion of the tube, an inlet and outlet in fluidic communication with the tube passage and an exterior of the microfluidic device, elements for vibrating the freestanding portion of the tube, and elements for sensing movement of the freestanding portion of the tube so as to measure the vibration frequency and/or deflection of the freestanding portion and produce therefrom at least one output corresponding to a property of a fluid flowing through the tube passage. The system and method further entail placing the microfluidic device in a flowing fluid so that a fraction of the fluid enters the tube passage, and processing the output of the device to compute a property of the fluid.

34 Claims, 4 Drawing Sheets

SYSTEM AND METHOD OF ASSESSING A PROPERTY OF A FLOWING FLUID

CROSS REFERENCE TO RELATED APPLICATIONS

This application claims the benefit of U.S. Provisional Application No. 61/005,677, filed Dec. 7, 2007. The contents of this prior application are incorporated herein by reference.

BACKGROUND OF THE INVENTION

The present invention generally relates to fluid sensing devices and methods of using such devices. More particularly, this invention relates to a micromachined fluid sensing device capable of measuring properties of a fluid in a fluid system that exceeds the internal flow capacity of the device.

Processes and designs for resonant mass flow and density sensors using silicon micromachining techniques are disclosed in commonly-assigned U.S. Pat. Nos. 6,477,901, 6,647,778, 7,228,735 and 7,263,882, as well as GB 2,221, 302A, and WO2007/147786 A1. As used herein, micromachining is a technique for forming very small elements by bulk etching a substrate (e.g., a silicon wafer), or by surface thin-film etching, the latter of which generally involves depositing a thin film (e.g., polysilicon or metal) on a sacrificial layer (e.g., oxide layer) on a substrate surface and then selectively removing portions of the sacrificial layer to free the deposited thin film. In the processes disclosed by U.S. Pat. No. 6,477,901 to Tadigadapa et al. and U.S. Pat. No. 6,647,778 to Sparks, wafer bonding and silicon etching techniques are used to produce microelectromechanical systems (MEMS) comprising one or more suspended silicon tubes on a wafer. The tube is vibrated at resonance, by which the flow rate and density of a fluid flowing through the tube can be determined.

Sensors of the type taught by the above-noted U.S. patents have found use in a variety of applications. A notable advantage of these sensors is the extremely miniaturized scale to which they can be fabricated, which among other things enables the sensors to precisely analyze very small quantities of fluids. However, in certain applications where relatively large volume flow rates exist, the limited flow capacity of these miniaturized sensors can be inadequate. Nonlimiting examples include industrial applications in which the flow of petrochemicals, gases, water, air, and other liquids flow through relative large pipes that can be a meter or more in diameter. Other nonlimiting examples include fluid flows in automotive and aerospace applications, including air intake, petrochemical fuels, hydrogen, alcohols, etc. Existing flow sensors typically utilize hot-wire and drag-force technology. However, it would be desirable if sensors of the type taught by Tadigadapa et al. and Sparks could be adapted for relatively high flow applications without necessitating an increase in sensor size.

BRIEF SUMMARY OF THE INVENTION

The present invention provides a fluid sensing system and method for sensing properties of a flowing fluid with the use of a microfluidic device, in which the fluid sensing system is configured to measure properties of the fluid though the fluid flow volume exceeds the internal flow capacity of the microfluidic device.

According to a first aspect of the invention, the microfluidic device of the fluid sensing system comprises a micromachined tube supported above a substrate so as to define a gap therebetween, a tube passage within a freestanding portion of the micromachined tube, an inlet and outlet in fluidic communication with the tube passage and an exterior of the microfluidic device, means for vibrating the freestanding portion of the micromachined tube at a resonant frequency thereof, and means for sensing movement of the freestanding portion of the micromachined tube so as to measure at least one of the vibration frequency and deflection of the freestanding portion relative to the substrate and produce therefrom at least one output corresponding to at least one of the mass flow rate, specific gravity, and density of a fluid flowing through the tube passage. The fluid sensing system further includes means for placing the microfluidic device in a flowing fluid so that a fraction of the fluid enters the tube passage of the micromachined tube through the inlet of the microfluidic device, and means for processing the at least one output to compute a property of the fluid.

According to a second aspect of the invention, the method entails providing a microfluidic device as described above, placing the microfluidic device in a flowing fluid so that a fraction of the fluid enters the tube passage of the micromachined tube through the inlet of the microfluidic device, and the at least one output is processed to compute a property of the fluid.

The method and fluid system of this invention are well suited for a variety of applications involving large volumes of flowing fluids, and are capable of determining a variety of properties of such fluids, such as volumetric flow rate, mass flow rate, specific gravity, and/or density. The determination of specific gravity and density can be used to obtain the relative chemical concentrations of constituents of the fluid, and detect the presence of undesirable constituents such as gas bubbles in a liquid, solid particles in a liquid or gas, etc. The system and method can be utilized in a variety of applications, including industrial facilities and land-based, aquatic-based, and aerospace vehicles. Notable examples of fluids that can be assessed with the present invention include liquid and gaseous fuels, air, water, lubricants, hydraulic fluids including transmission and brake fluids, coolants, engine exhaust gases, etc.

Other objects and advantages of this invention will be better appreciated from the following detailed description.

DETAILED DESCRIPTION OF THE INVENTION

Figure 1:
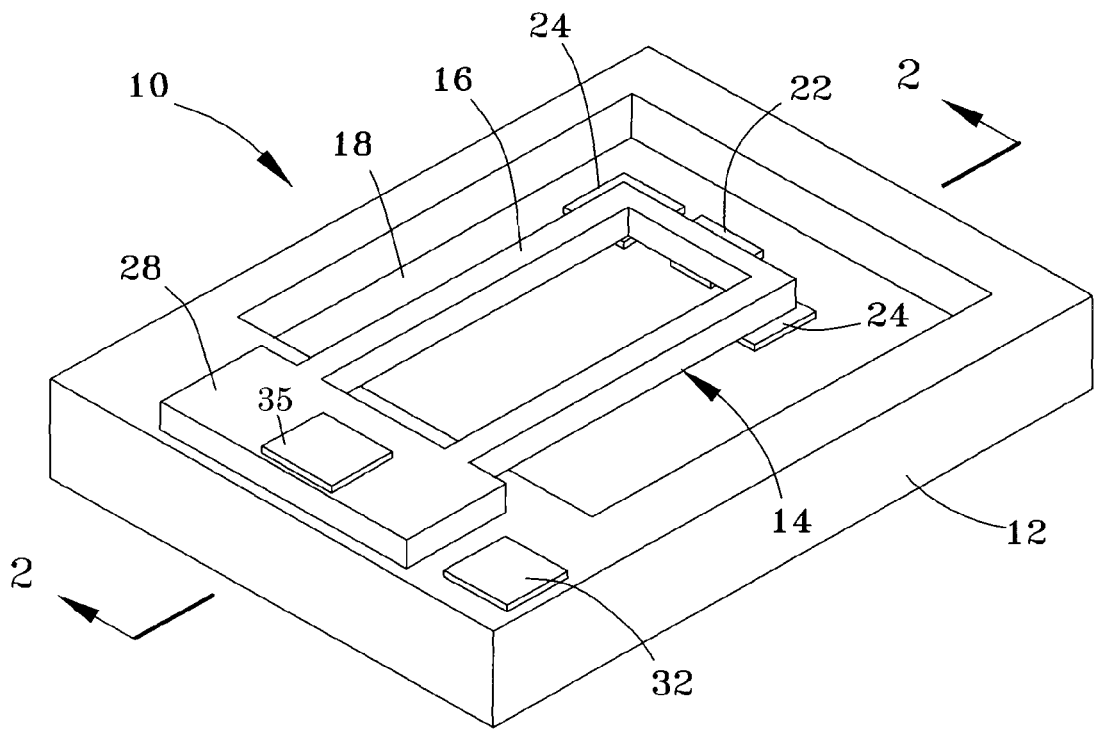
FIGS. 1 and 2 are perspective and cross-sectional views, respectively, of a microfluidic device with a resonating micromachined tube through which a fluid flows in accordance with the prior art and the present invention.
Figure 2:
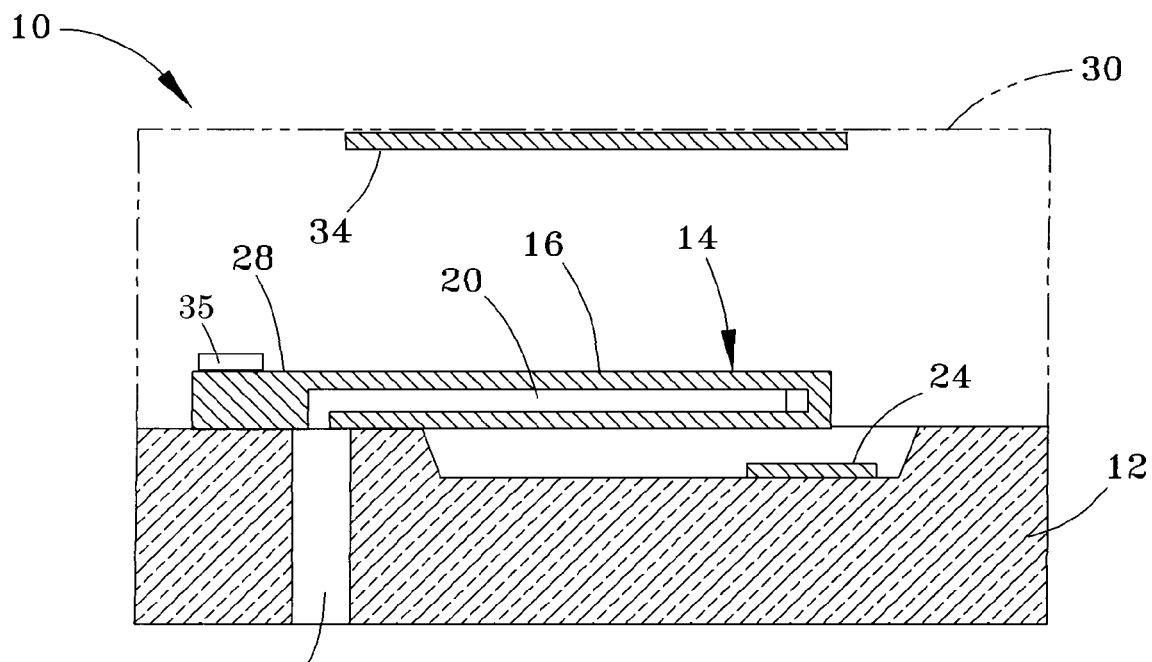

FIGS. 1 and 2 represent a microfluidic device 10 of a type disclosed in commonly-assigned U.S. Pat. No. 6,477,901 to Tadigadapa et al., and suitable for use with the present invention. Tadigadapa et al., whose contents relating to the fabrication and operation of a Coriolis-based sensor are incorporated herein by reference, disclose processes and designs for flow sensing devices of the type shown in FIG. 1 using micromachining techniques. In the processes disclosed by Tadigadapa et al., wafer bonding and silicon etching techniques can be used to produce microelectromechanical systems (MEMS) comprising one or more suspended micromachined tubes through which one or more fluids flow. The tube is vibrated at or near resonance, by which certain properties of the fluid, including flow rate and density, can be ascertained using Coriolis force principles. Notable advantages of these sensors include the extremely miniaturized scale to which they can be fabricated and their ability to precisely analyze very small quantities of fluids. As will be understood from the following description, the precision of such sensors is also advantageous in the present invention.

The microfluidic device 10 represented in FIGS. 1 and 2 includes a micromachined tube 14 extending from a base 28 on a substrate 12, with a freestanding portion 16 of the tube 14 suspended above a surface 18 of the substrate 12 to define a gap therebetween. The substrate 12 may be formed of silicon or another semiconductor material, quartz, glass, ceramic, metal, a polymeric material, a composite material, etc. The tube 14 may be micromachined from silicon, doped silicon or another semiconductor material, silicon carbide, quartz or another glass material, ceramic materials, metallic materials, and composite materials. The substrate 12 and tube 14 can be fabricated separately, after which the tube 14 is attached as a unitary member to the surface 18 of the substrate 12. The freestanding portion 16 of the tube 14 is generally U-shaped, though other shapes—both simpler and more complex—are also within the scope of this invention, such as straight, omega, S, or Z-shaped, etc. Notable examples include tube shapes disclosed in commonly assigned U.S. patent application Ser. Nos. 11/620,411, 11/620,908, 12/143,942, and 12/267,263, whose contents are incorporated herein by reference. Furthermore, if the fluid to be sensed is a gas, the tube 14 can be configured to utilize stiffening bars, tube shapes, rounded corners, and thick walls to improve the performance of the tube 14 for gas flow applications. As taught in Ser. No. 12/267,263, high gas flow rates may cause the micromachined tube 14 to vibrate in alternative modes at frequencies different that would occur if a liquid was being evaluated. This phenomenon is believed to be due to much lower internal fluidic damping of the tube 14 with gases as compared to liquids. To avoid alternative vibration modes, the tube 14 can incorporate one or more crossbars to stiffen the tube 14 and thereby reduce the likelihood of an alternate resonate mode developing during gas flow through the tube 14.

FIGS. 1 and 2 further depict drive and sensing electrodes 22 and 24 located on the substrate surface 18 beneath the freestanding portion 16 of the tube 14, and bond pads 32 (only one of which is shown) for transmitting input and output signals to and from the device 10. With a fluid entering the device 10 through a port 26 and flowing through an internal passage 20 within the tube 14, the freestanding portion 16 can be vibrated by the drive electrode 22 to ascertain certain properties of the fluid, such as flow rate and density, using Coriolis force principles. In particular, the freestanding portion 16 is vibrated in a direction perpendicular to the surface 18 of the substrate 12, preferably at or near its resonant frequency. During half of the vibration cycle in which the tube 14 moves upward, the freestanding portion 16 has upward momentum as the fluid travels around the tube bends, and the fluid flowing out of the freestanding portion 16 resists having its vertical motion decreased by pushing up on that part of the freestanding portion 16 nearest the fluid outlet. The resulting force causes the freestanding portion 16 of the tube 14 to twist about the axis of symmetry of the freestanding portion 16, which is parallel to the legs of the freestanding portion 16. As the tube 14 moves downward during the second half of its vibration cycle, the freestanding portion 16 twists in the opposite direction. This twisting characteristic is referred to as the Coriolis effect, and the degree to which the freestanding portion 16 of the tube 14 deflects during a vibration cycle as a result of the Coriolis effect can be correlated to the mass flow rate of the fluid flowing through the tube 14, while the density of the fluid is inversely proportional to the square of the vibration frequency at resonance. The resonant frequency of the tube 14 is controlled by its mechanical design (shape, size, construction and materials). Typical resonant frequencies for the micromachined tube 14 represented in FIGS. 1 and 2 will generally be in the range of about 1 kHz to about 100 kHz. The amplitude of vibration can be adjusted through the drive electrode 22 located beneath the tube 14. If formed of doped silicon, the tube 14 can serve as an electrode that can be capacitively coupled to the drive electrode 22, enabling the drive electrode 22 to capacitively (electrostatically) drive the tube 14. If the tube 14 is formed of a nonconductive material, a separate electrode can be formed on the tube 14 opposite the drive electrode 22 for vibrating the tube 14 electrostatically. An alternative driving technique is to provide a piezoelectric element on an upper surface of the tube 14 to generate alternating forces in the plane of the tube 14 that flex the freestanding portion 16 of the tube 14 in directions normal to the plane of the tube 14. Other alternatives are to drive the freestanding portion 16 of the tube 14 magnetically, thermally, or by another actuation technique. The sensing electrodes 24 provide feedback to the drive electrode 22 to enable the vibration frequency to be controlled with appropriate circuitry, while also sensing the deflection of the tube 14 relative to the substrate 12. The sensing electrodes 24 can sense the tube 14 capacitively or in any other suitable manner capable of sensing the proximity or motion of the tube 14.

In FIG. 2, the microfluidic device 10 is schematically shown as enclosed by a cap 30 to form a sensing package. The cap 30 allows for vacuum packaging that reduces air damping of the tube vibration. A variety of package and wafer-level methods exist and are well known for vacuum packaging electronic devices, and therefore will not be discussed here in any detail. Such methods include solder or weld hermetic packages, and wafer bonding using glass frit, solder, eutectic alloy, adhesive, and anodic bonding. A suitable material for the cap 30 is silicon, though it is foreseeable that a variety of other materials could be used including metals and glass materials, the latter including borosilicate glass (e.g., Pyrex). In preferred embodiments of this invention, the bond between the cap 30 and the substrate 12 is hermetic, and the enclosure formed by the substrate 12 and cap 30 is evacuated to enable the tube 14 to be driven efficiently at high quality (Q) values without damping, for example, Q values of about 10,000 to about 64,000 when the tube 14 is filled with air. In such an embodiment, a getter material 34 is preferably placed in the enclosure to assist in reducing and maintaining a low cavity pressure. As an alternative to a hermetically sealed package, the tube 14 could be enclosed such that a vacuum can be drawn when desired through the use of a pump.

Properties such as densities of materials change with temperature, as do the Young's and shear moduli of materials. For this reason, the device 10 may further include elements for measuring the temperature of the fluid flowing through the tube 14. For example, FIG. 1 shows a temperature-sensing element 35 placed on the base 28 of the tube 14 to enable the temperature of the tube 14 and its fluid contents to be monitored with suitable accuracy under many operating conditions. Changes in mechanical properties of the tube 14 and properties of the fluid therein attributable to temperature changes can then be compensated for with appropriate circuitry (not shown). A suitable temperature-sensing element 35 can be constructed in accordance with known practices, for example, one or more metal layers of the type employed to form the electrodes 22 and 24 and bond pads 32 and their associated conductive runners. Alternatively or in addition, an electrical potential could be applied to pass a current through the tube 14 to raise and maintain the temperature of the tube 14 and the fluid flowing therethrough by Joule heating, with the temperature-sensing element 35 used as feedback for appropriate control circuitry (not shown).

The shape and size of the tube 14 are preferably chosen to provide a suitable flow capacity and have suitable vibration parameters for the fluid to be evaluated with the microfluidic device 10. Because micromachining technologies are employed to fabricate the tube 14, the size of the tube 14 can be extremely small, such as lengths of about 0.5 mm and cross-sectional areas of about 250 square micrometers, with smaller and larger tubes also being within the scope of this invention. Because of the ability to produce the tube 14 at such miniaturized sizes, the device 10 can be used to process very small quantities of fluid for analysis. This miniaturization can render the device 10 unsuited for applications in which measurements of properties are desired for a fluid flowing at relatively high flow rates or within a large passage.

Figure 3:
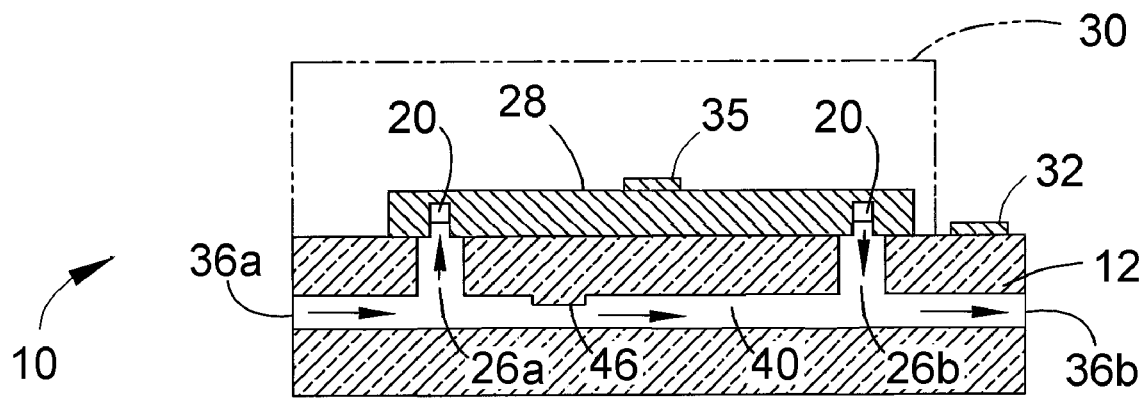
FIG. 3 is cross-sectional view of the fluid sensing device of FIGS. 1 and 2 modified to include a bypass in accordance with an embodiment of this invention.
Figure 4:
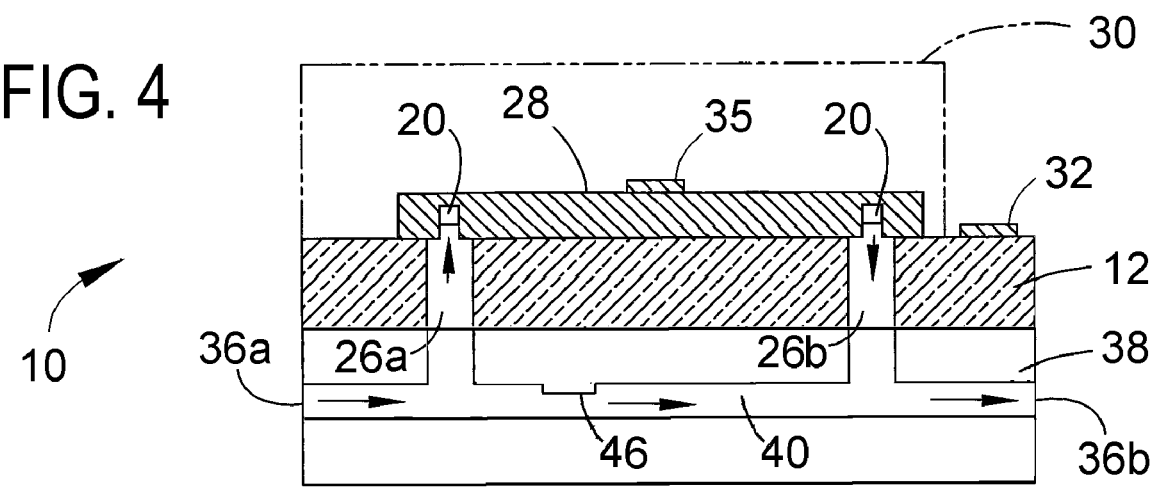
FIG. 4 is cross-sectional view of the fluid sensing device of FIGS. 1 and 2 modified to include a bypass in accordance with a second embodiment of this invention.

FIGS. 3 and 4 represent cross-sectional views of the microfluidic device 10 of FIGS. 1 and 2 modified in accordance with embodiments of the invention (FIGS. 3 and 4 correspond to a cross-section of the device 10 through the base 28 and transverse to the cross-section of FIG. 2). Fluid enters and leaves each of the devices 10 through separate fluid inlet and outlet passages 36a and 36b that fluidically communicate with the exterior of the device 10 as well as ports 26a and 26b (commonly identified with reference number 26 in FIG. 2) through which the fluid flows when entering and leaving the tube 14. Each device 10 is further configured to have an internal bypass passage 40 fluidically in parallel with the passage 20 through the tube 14, therefore allowing excess fluid entering the device 10 through the inlet passage 36a to be routed directly to the outlet passage 36b instead of through the tube 14.

The inlet and outlet passages 36a and 36b and bypass passage 40 may be defined entirely within the bulk of the substrate 12 as shown in FIG. 3, or within a separate substrate 38 attached to the substrate 12 as shown in FIG. 4. Alternatively, the passage 40 may be partially or entirely defined by a gap between the substrate 12 and the base 28 of the tube 14. The bypass passage 40 is preferably formed to have a protrusion 46 that acts as a flow restrictor, thereby ensuring adequate flow through the passage 20 of the tube 14. To provide a suitable bypass functionality, the remainder of the bypass passage 40 preferably has a cross-sectional area greater than that of the passage 20 within the tube 12.

Figure 5:
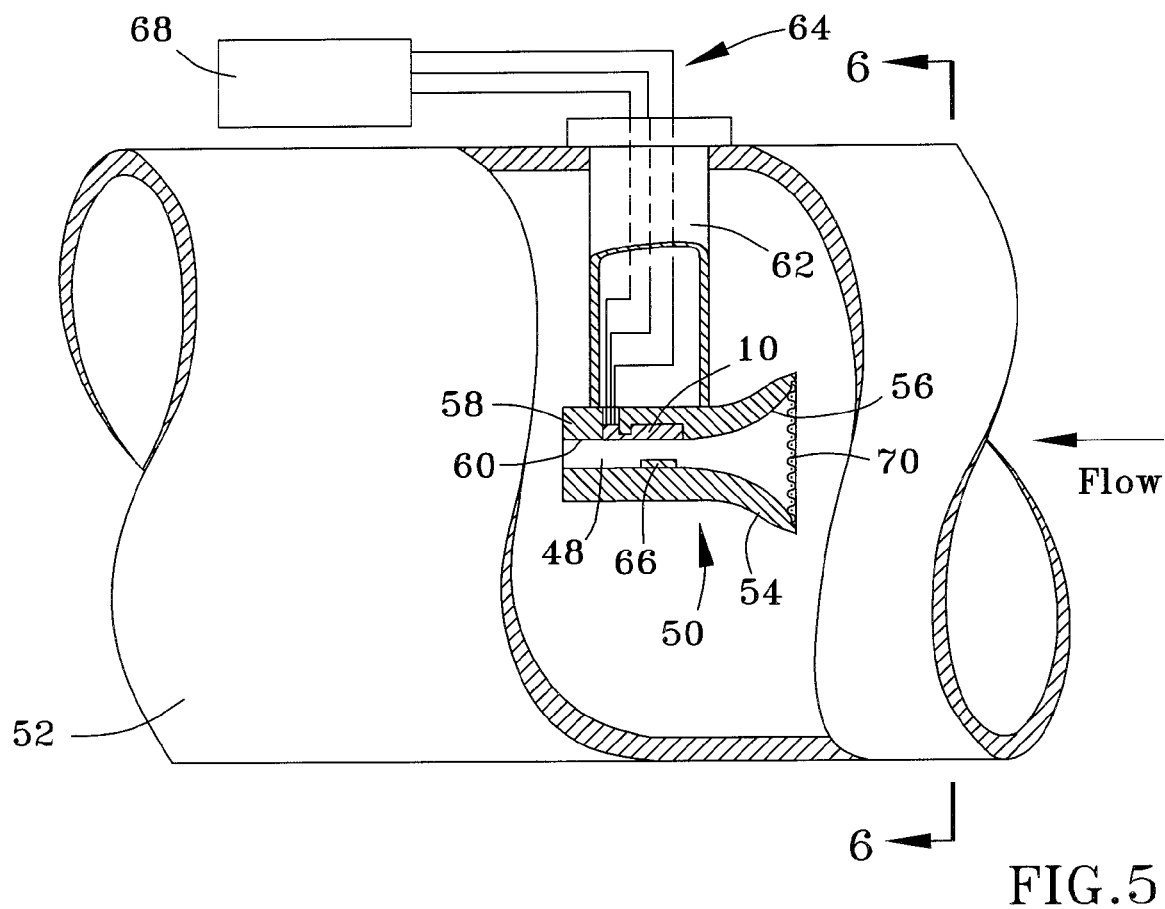
FIG. 5 is a longitudinal cross-sectional view schematically representing a large fluid flow system in which the fluid sensing device of FIG. 3 or 4 is placed with an apparatus configured in accordance with another embodiment of this invention.

The microfluidic devices 10 represented in FIGS. 3 and 4 can be used to evaluate a variety of fluids, including gases and liquids. Of particular interest to the present invention are fluids flowing through passages substantially larger than the passages 20, 36a, 36b, and 40 within the device 10. Nonlimiting examples include industrial facilities in which petrochemicals, gases, water, air, and other fluids flow through relative large pipes that may be a meter or more in diameter, and automotive and aerospace applications that entail flowing fluids such as liquid and gaseous fuels including petrochemicals, hydrogen and alcohols, intake air, water, lubricants, hydraulic fluids including transmission and brake fluids, coolants, engine exhaust gases, etc. According to an aspect of the invention, the microfluidic device 10 can be used to sense fluid properties in such situations by being mounted within a protective housing that can be placed in the flowing fluid so that the entrance to the inlet passage 36a is oriented to face upstream. For example, the device 10 could be configured as shown in FIG. 4 and mounted so that the substrate 38 protrudes through an opening in the wall of a conduit through which a fluid to be sensed flows, with the inlet passage 36a facing upstream into the fluid flow. Another example represented in FIGS. 5 and 6 allows the device 10 to be placed farther into the flow stream within a conduit 52. In FIG. 5, the device 10 is shown as mounted in an interior surface of a flow passage 48 within a funnel 50, which generally serves the role of the substrate 38 in FIG. 4. The funnel 50 is preferably axisymmetric and represented as axially aligned with the direction of fluid flow through the conduit 52, which may be a large pipe, channel, or other relatively large fluid-containing passage. An upstream end 54 of the funnel 50 has an inlet 56 that is larger in cross-section than an outlet 60 located at a downstream end 58 of the funnel 50. The size of the inlet 56 is intended to promote fluid flow through the passage 48 under various flow conditions. While FIG. 5 shows the inlet 56 as having a curved cross-sectional shape, other cross-sectional shapes could be used.

Figure 6:
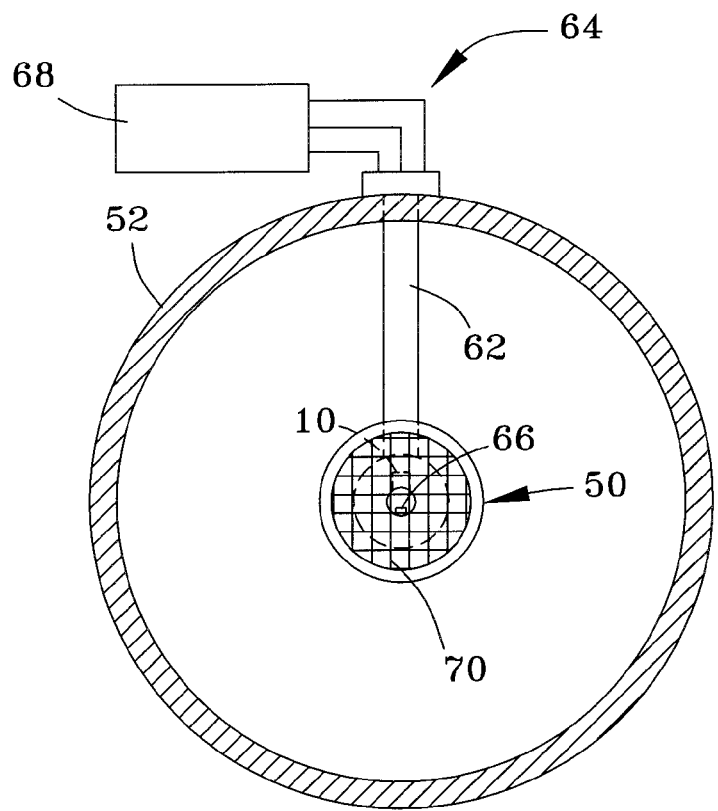
FIG. 6 is a diametrical cross-sectional view along section line 6-6 of FIG. 5.

The funnel 50 is supported within the conduit 52 with a truss 62, which preferably places the funnel 50 away from the wall of the conduit 52 where boundary layer conditions are likely to exist. To minimize disturbances in the flow field, the truss 62 can be configured to have a teardrop-shaped cross-section, with the blunt end of the truss 62 facing upstream. In FIGS. 5 and 6, the funnel 50 is shown placed near the center of the pipe 52 where the maximum fluid flow velocity is likely to exist under fully laminar flow conditions within the conduit 52. Wiring 64 is passed through the truss 62 to the funnel 50, where electrical connections are made to the microfluidic device 10. Similar to the protrusion 46 within the bypass passage 40 of FIGS. 3 and 4, the passage 48 within the funnel 50 can also contain a protrusion 66 located diametrically opposite the device 10 to promote the flow of fluid from the passage 48 and into the inlet passage 36a of the device 10. The inlet passage 36a may be oriented transverse or parallel to the axis of the funnel 50. Alternatively, it is foreseeable that the microfluidic device 10 of FIGS. 1 and 2 could be used with the funnel 50, in which case the bypass passage 40 is omitted and flow to and from the tube 14 would be directly through the ports 26a and 26b. However, an advantage of the devices 10 shown in FIGS. 3 and 4 is believed to be a reduced risk that particles suspended in the fluid will enter the tube 14. The risk of damage from suspended particles can be further reduced by placing a screen 70 at the entrance to the inlet 56, as shown in FIGS. 5 and 6.

FIGS. 5 and 6 show a processing unit 68 mounted separately from the device 10 and outside the conduit 52, such that the unit 68 is not subject to hostile environmental and/or chemical conditions that may exist within the conduit 52. Furthermore, in the case of assessing combustive fluids and gases, placement of the unit 68 outside the conduit 52 reduces the risk of explosion or fire while allowing the lower-voltage device 10 to be placed in the fluid. While the unit 68 is represented as connected to a single device 10, multiple devices 10 could be connected and monitored by the unit 68. Based on the motion of the freestanding portion 16 of the tube 14 sensed by the sensing electrodes 24, the device 10 produces one or more outputs corresponding to at least the density of the fluid flowing through the tube 14, and optionally the mass flow rate, volumetric flow rate, specific gravity, etc., of the fluid. Circuitry within the processing unit 68 can then be used to compute fluid density and/or other optional properties of the fluid, including chemical concentrations if the fluid is a mixture.

Figure 7:
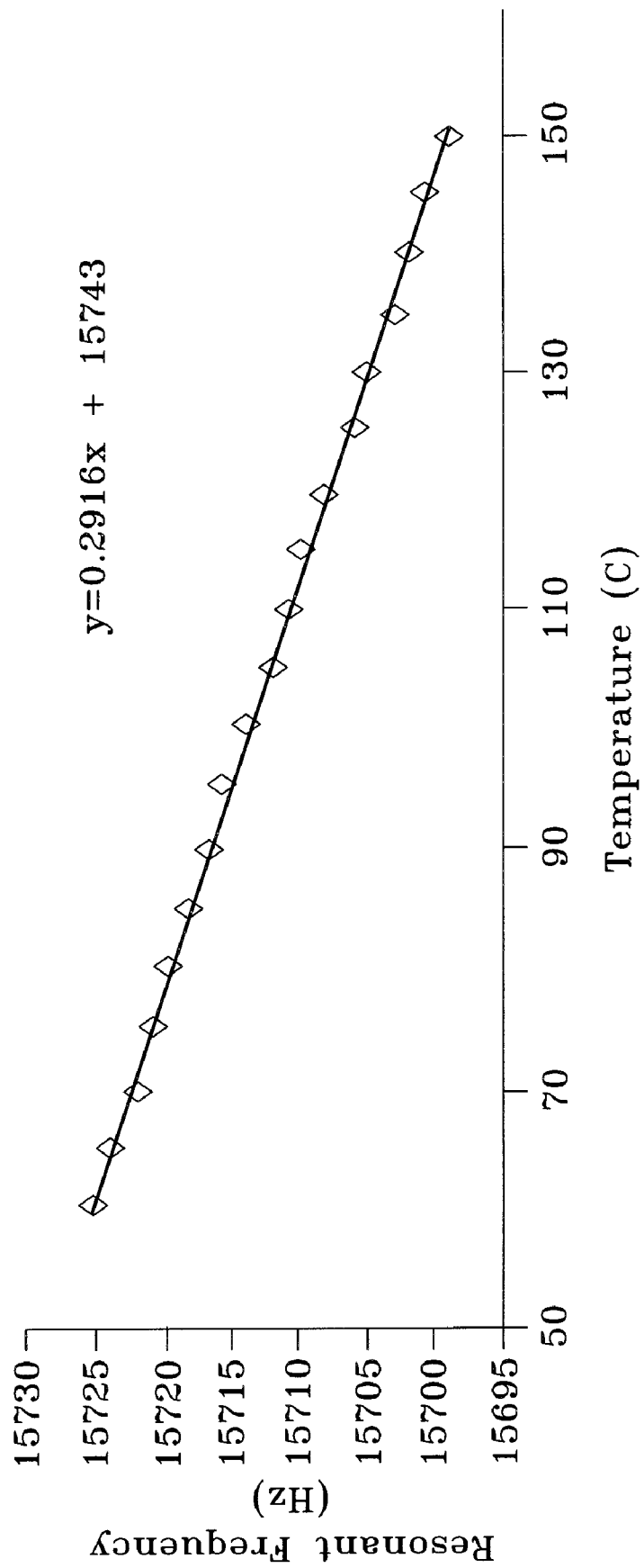
FIG. 7 is a graph plotting the effect of temperature on the performance of a fluid sensing device of the type shown in FIGS. 1 through 4 when installed in a fluid flow system as represented in FIGS. 5 and 6.

FIG. 7 is a graph plotting the resonant frequency of a microfluidic device of the types shown in FIGS. 1 through 4 against temperature. FIG. 7 evidences the operational capability of the devices 10 at temperatures of at least 150° C., as well as a linear relationship between resonant frequency and temperature. As such, the microfluidic devices 10 of this invention are capable of being immersed in flowing fluids over a broad range of temperatures.

As represented in FIGS. 3 through 6, the devices 10 are configured for use in a wide variety of fluid systems, including industrial and vehicular applications whose fluid systems exceed the capacity of the micromachined tube 14. Furthermore, a variety of fluid properties can be measured with the devices 10, including but not limited to flow rate (including mass and volumetric flow rates), density and properties that can be correlated to density, such as specific gravity, relative chemical concentrations of fluid constituents. The devices 10 can also be employed to sense the presence of undesirable contaminants, such as liquids (e.g., fuel and water in engine oil), gas or air bubbles (e.g., in fuels and brake fluids), solid particles (e.g., in engine oil), etc.

While the invention has been described in terms of certain embodiments, it is apparent that other forms could be adopted by one skilled in the art, and the scope of the invention is to be limited only by the following claims.

The invention claimed is:

1. A fluid sensing system adapted to be placed in a flowing fluid for sensing properties thereof, the fluid sensing system comprising:
 a microfluidic device comprising a micromachined tube supported above a substrate so as to define a gap therebetween, a tube passage within a freestanding portion of the micromachined tube, an inlet and outlet in fluidic communication with the tube passage and an exterior of the microfluidic device, means for vibrating the freestanding portion of the micromachined tube at a resonant frequency thereof, and means for sensing movement of the freestanding portion of the micromachined tube so as to measure at least one of the vibration frequency and deflection of the freestanding portion relative to the substrate and produce therefrom at least one output corresponding to at least one of the mass flow rate, specific gravity, and density of a fluid flowing through the tube passage;
 means for placing the microfluidic device in a flowing fluid so that a fraction of the fluid enters the tube passage of the micromachined tube through the inlet of the microfluidic device; and
 means for processing the at least one output to compute a property of the fluid.

2. The fluid sensing system according to claim 1, wherein the microfluidic device further comprises a bypass passage fluidically in parallel with the tube passage through the micromachined tube.

3. The fluid sensing system according to claim 2, wherein the microfluidic device further comprises a protrusion within the bypass passage to promote fluid flow away from the bypass passage and into the tube passage of the micromachined tube.

4. The fluid sensing system according to claim 1, wherein the placing means is configured for mounting the microfluidic device in an opening in a wall of a conduit so as to place at least the inlet of the microfluidic device in a fluid flowing through the conduit.

5. The fluid sensing system according to claim 1, wherein the placing means is configured for mounting the microfluidic device away from a wall of a conduit so as to place the microfluidic device in a fluid flowing through the conduit.

6. The fluid sensing system according to claim 5, wherein the placing means is configured for mounting the microfluidic device outside the fluid flow boundary layer within the conduit.

7. The fluid sensing system according to claim 5, wherein the placing means comprises a funnel having a funnel passage therethrough and a truss for positioning the funnel away from the wall of the conduit.

8. The fluid sensing system according to claim 7, wherein the funnel has an upstream end defining a funnel inlet and a downstream end defining a funnel outlet, and the funnel inlet has a larger cross-section than the funnel outlet to promote fluid flow through the funnel passage.

9. The fluid sensing system according to claim 7, wherein the microfluidic device is disposed in a surface of the funnel defining the funnel passage so as to place at least the inlet of the microfluidic device in the fluid flowing through the funnel passage.

10. The fluid sensing system according to claim 7, further comprising a screen disposed at the funnel inlet of the funnel for excluding particles from the funnel passage.

11. The fluid sensing system according to claim 1, wherein the fluid sensing system is installed in a conduit of an industrial facility or a land-based, aquatic-based, or aerospace vehicle.

12. The fluid sensing system according to claim 1, wherein the fluid is chosen from the group consisting of liquid and gaseous fuels, air, water, lubricants, hydraulic fluids, coolants, and engine exhaust gases.

13. The fluid sensing system according to claim 1, wherein the property of the fluid is chosen from the group consisting of mass and volumetric flow rate, density, specific gravity, relative chemical concentrations of fluid constituents, and the presence of gaseous, liquid, and solid contaminants.

14. A fluid sensing system installed in a conduit for sensing properties of a fluid flowing through the conduit, the fluid sensing system comprising:
 a microfluidic device comprising a micromachined tube supported above a substrate so as to define a gap therebetween, a tube passage within a freestanding portion of the micromachined tube, an inlet and outlet in fluidic communication with the tube passage and an exterior of the microfluidic device, means for vibrating the freestanding portion of the micromachined tube at a resonant frequency thereof, and means for sensing movement of the freestanding portion of the micromachined tube so as to measure at least one of the vibration frequency and deflection of the freestanding portion relative to the substrate and produce therefrom at least one output corresponding to at least one of the mass flow rate, specific gravity, and density of a fluid flowing through the tube passage;

means for mounting the microfluidic device to the conduit and placing the microfluidic device in the fluid flowing through the conduit so that a fraction of the fluid enters the tube passage of the micromachined tube through the inlet of the microfluidic device; and means for processing the at least one output to compute a property of the fluid.

15. The fluid sensing system according to claim 14, wherein the microfluidic device further comprises a bypass passage fluidically in parallel with the tube passage through the micromachined tube.

16. The fluid sensing system according to claim 15, wherein the microfluidic device further comprises a protrusion within the bypass passage to promote fluid flow away from the bypass passage and into the tube passage of the micromachined tube.

17. The fluid sensing system according to claim 14, wherein the mounting means mounts the microfluidic device in an opening in a wall of the conduit and places at least the inlet of the microfluidic device in the fluid flowing through the conduit.

18. The fluid sensing system according to claim 14, wherein the mounting means mounts the microfluidic device away from a wall of the conduit and places the microfluidic device in the fluid flowing through the conduit.

19. The fluid sensing system according to claim 18, wherein the mounting means mounts the microfluidic device outside the fluid flow boundary layer within the conduit.

20. The fluid sensing system according to claim 18, wherein the mounting means comprises a funnel having a funnel passage therethrough and a truss for positioning the funnel away from the wall of the conduit.

21. The fluid sensing system according to claim 20, wherein the funnel has an upstream end defining a funnel inlet and a downstream end defining a funnel outlet, and the funnel inlet has a larger cross-section than the funnel outlet to promote fluid flow through the funnel passage.

22. The fluid sensing system according to claim 20, wherein the microfluidic device is disposed in a surface of the funnel defining the funnel passage so as to place at least the inlet of the microfluidic device in the fluid flowing through the funnel passage.

23. The fluid sensing system according to claim 20, further comprising a screen disposed at the funnel inlet of the funnel for excluding particles from the funnel passage.

24. The fluid sensing system according to claim 14, wherein the microfluidic device is located entirely inside the conduit.

25. The fluid sensing system according to claim 14, wherein the processing means is located entirely outside the conduit.

26. The fluid sensing system according to claim 14, wherein the conduit is installed in an industrial facility or a land-based, aquatic-based, or aerospace vehicle.

27. The fluid sensing system according to claim 14, wherein the fluid is chosen from the group consisting of liquid and gaseous fuels, air, water, lubricants, hydraulic fluids, coolants, and engine exhaust gases.

28. The fluid sensing system according to claim 14, wherein the property of the fluid is chosen from the group consisting of mass and volumetric flow rate, density, specific gravity, relative chemical concentrations of fluid constituents, and the presence of gaseous, liquid, and solid contaminants.

29. A method of sensing properties of a flowing fluid, the method comprising:

providing a microfluidic device comprising a micromachined tube supported above a substrate so as to define a gap therebetween, a tube passage within a freestanding portion of the micromachined tube, an inlet and outlet in fluidic communication with the tube passage and an exterior of the microfluidic device, means for vibrating the freestanding portion of the micromachined tube at a resonant frequency thereof, and means for sensing movement of the freestanding portion of the micromachined tube so as to measure at least one of the vibration frequency and deflection of the freestanding portion relative to the substrate and produce therefrom at least one output corresponding to at least one of the mass flow rate, specific gravity, and density of a fluid flowing through the tube passage;

placing the microfluidic device in the flowing fluid so that a fraction of the fluid enters the tube passage of the micromachined tube through the inlet of the microfluidic device; and processing the at least one output to compute a property of the fluid.

30. The method according to claim 29, wherein the microfluidic device is located entirely within the fluid.

31. The method according to claim 29, wherein means for performing the processing step is located entirely outside the fluid.

32. The method according to claim 29, wherein the method is performed in an industrial facility or a land-based, aquatic-based, or aerospace vehicle.

33. The method according to claim 29, wherein the fluid is chosen from the group consisting of liquid and gaseous fuels, air, water, lubricants, hydraulic fluids, coolants, and engine exhaust gases.

34. The method according to claim 29, wherein the property of the fluid is chosen from the group consisting of mass and volumetric flow rate, density, specific gravity, relative chemical concentrations of fluid constituents, and the presence of gaseous, liquid, and solid contaminants.

* * * * *